United States Patent [19]

Malinoff

[11] Patent Number: 4,565,100
[45] Date of Patent: Jan. 21, 1986

[54] PIPETTE DEVICE
[75] Inventor: Don W. Malinoff, Granada Hills, Calif.
[73] Assignee: Culture-Tek, Granada Hills, Calif.
[21] Appl. No.: 491,305
[22] Filed: May 3, 1983

Related U.S. Application Data

[63] Continuation-in-part of Ser. No. 307,745, Oct. 2, 1981, Pat. No. 4,468,974.

[51] Int. Cl.⁴ .............................................. B01L 3/02
[52] U.S. Cl. .............................. 73/863.32; 73/864.11; 422/100
[58] Field of Search ........... 73/863.32, 864.11, 864.14; 422/100

[56] References Cited
U.S. PATENT DOCUMENTS 3,696,971 10/1972 Maclin ............................. 73/863.32
3,855,868 12/1974 Sudvaniemi ...................... 73/863.32
4,215,092 7/1980 Suovaniemi et al. ............ 73/863.32
4,335,621 6/1982 Tervamaki et al. .............. 73/863.32

Primary Examiner—Stewart J. Levy
Assistant Examiner—John E. Chapman, Jr.
Attorney, Agent, or Firm—Spensley Horn Jubas & Lubitz

[57] ABSTRACT

An improved pipette sampling system for removing and transferring a plurality of liquid samples to and from a multi-well tray is disclosed. A pipette sampling system comprises a housing having elongated plates defining a first chamber therein. A patterned array of collector conduits is joined to the plates such that a first outwardly extending section extends into the chamber and a second outwardly extending section extends away from the chamber and towards the tray. A patterned array of tubular pipette tips are removably joined to and in flow communication with said array of collector conduits. The tips and conduits are designed to contain small, measured volumes of fluid.

13 Claims, 4 Drawing Figures

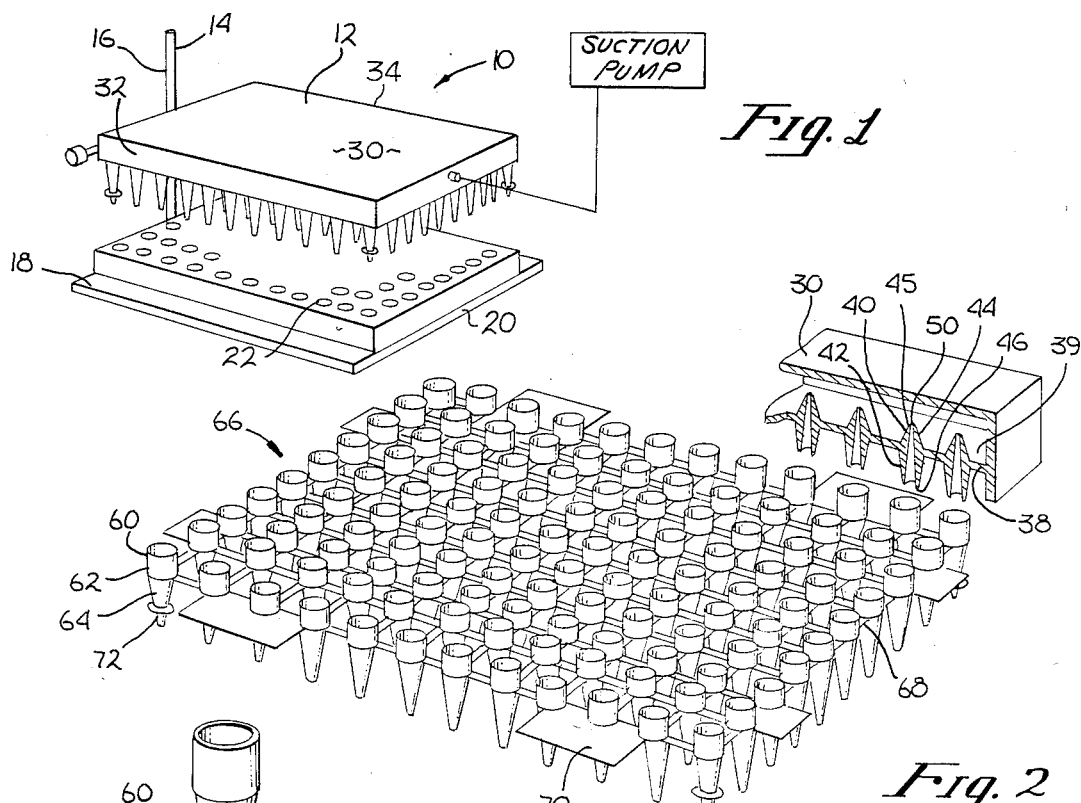

PIPETTE DEVICE

RELATED APPLICATIONS

This application is a continuation-in-part of application Ser. No. 307,745 filed Oct. 2, 1981, now U.S. Pat. No. 4,468,974.

BACKGROUND OF THE INVENTION

1. Field of the Invention

This invention relates to further improvements in pipette samplers and related systems.

2. Prior Art

The use of various sized and shaped pipettes for withdrawing liquid samples from a container so as to measure the same and transfer it to a second container, is well recognized in the prior art. One problem with such pipette is that in order to measure and transfer a given quantity of liquid, a great deal of care must be exercised in order to insure accuracy. While prior art methods are satisfactory, in terms of accuracy, they are very time consuming. Recent advances in the microbiological, immunological and other medical laboratory research have made such approach outmoded. This is because such system may require the container with the liquid to be measured and transferred to be open to the atmosphere each time the pipette is filled. In many procedures, continued and repeated exposure to the atmosphere can lead to poor results. Further, today mass sampling and testing is typically done. If individual samples had to be taken, even if there were no adverse consequences, the time factor using old methodologies and systems would slow research to a snail's pace.

The prior art has recognized these problems and has come up with a number of different systems which are alleged solutions. These devices are adapted to be used with multi-well trays, with a liquid sample in each well or in a tube disposed in each well. More recent devices are adapted to simultaneously withdraw a relatively large number of samples from the individual tubes or wells which contain the sample. Devices of such type are shown in U.S. Pat. Nos. 3,982,438; 4,158,053; 3,261,208; and 3,568,735. A review of these patents, however, will illustrate that while a solution is provided to the transfer of fluid from multi-well laboratory trays such are now extensively used in microbiological and immunological laboratory work, they are relatively complex and expensive.

One solution to the problem associated with these prior art devices is shown in my co-pending application Ser. No. 307,745, which is herein incorporated by reference. The pipette sampler system of the present invention represents yet a further improvement over the prior art and the previous application, in that it provides a method for sampling without the complexity or expense associated with prior art devices, but enables the system to be adapted such that various sized samples may be taken.

SUMMARY OF THE INVENTION

The present invention pipette sampler system has particular utility in microbiological laboratory settings such as those used in antibody research, cloning, assay technology and the like. The following broad description of the invention is set forth in a laboratory setting so as to provide some insight in how the device and system of the present invention can be used. Broadly speaking, the pipette sampler of the present invention is designed to separately remove a predetermined amount of fluid from a 96-well micro-culture dish or tray and transfer the volume removed to another 96-well tray in one operation. Such 96-well trays are well known and used throughout this industry. In a typical laboratory setting in antibody research, cell fusion is used to produce hybrids which in turn are used to produce antibodies. Antibodies are produced and the supernatant of the cell culture performed in the 96-well micro-culture trays. 150 micro-liter cultures are usually established from which fifty (50) micro-liter aliquots are to be removed periodically and assayed for the production of specific antibodies. This should be accomplished rapidly and efficiently to insure sterility of the original culture which should be maintained after each sampling. Further, the sampler must either be disposable or sterilized to insure the integrity of the research. As stated above, the complexity of the prior art devices is such that they do not appear to be disposable as is the device of the present invention. Further, complexity would also appear to make their disposal after each use very uneconomical. The device of the present invention can be used in situations where the prior art devices are used, but have the additional benefit of being particularly adapted for use with any micro-culture system where sampling is required and sterility is to be maintained between each sample taken. In addition, the system of the present invention enables various quantities to be withdrawn such that different sized samples may be taken without the need for purchasing different sized samplers.

In order to achieve these and other goals, the pipette sampler of the present invention comprises a housing having a top member, side and end members, and a generally flat plate joined to the side and end members which, along with the top, define a first manifold chamber. A rectilinear array of elongated, outwardly extending collector conduits are disposed on the plate. The collector conduits have a first portion which is configured to be inserted into an associated pipette tip and a second portion which extends into the first manifold chamber. The first and second portions have coaxial openings for fluid flow, but the openings for fluid flow in the first portion is larger than the openings for fluid flow in the second portion.

A patterned array of tubular pipette tips is removably joined to and in flow communication with the patterned array of the collector conduits. The pipette tips are configured for insertion into an associated well on the multi-well tray. A port is provided on the housing in fluid communication with the first chamber whereby a vacuum can be created in the first chamber causing a pre-determined amount of liquid to flow into each of the pipette tips and each of the collector conduits. Because the openings for fluid flow in the first and second portions of the collector conduits as well as the pipettes are specifically selected, fluid can readily flow through the tips and into both sections of the collector conduits. However, once the fluid reaches the upper opening in the second portion of the conduit, little if any liquid will continue to flow therethrough.

The novel features which are believed to be characteristic of the invention, both as to its organization and methods of operation, together with further objectives and advantages thereof, will be better understood from the following description considered in connection with the accompanying drawings in which a presently preferred embodiment of the invention is illustrated by way of example. It is to be expressly understood, however, that the drawings are for the purpose of illustration and description only, and are not intended as a definition of the limits of the invention.

BRIEF DESCRIPTION OF THE DRAWINGS

FIG. 1 is a perspective view showing the pipette sampler and related system of the present invention.

FIG. 2 is a perspective view showing the patterned array of tubular pipette tips to be joined to an associated pipette sampler.

FIG. 3 is an enlarged partial perspective view showing a plate for joining the pipette tips to an associated pipette sampler.

FIG. 4 is an enlarged partial perspective view showing removal of the pipette tips from an associated pipette sampler.

DETAILED DESCRIPTION OF THE INVENTION

As discussed hereinabove, the present invention is directed to a pipette sampler and related system for removing a plurality of liquid samples from multi-well tray. Referring first to FIG. 1, the entire system 10 is illustrated. The system 10 includes a pipette sampler 12 mounted on a stand 14, and more specifically onto a post 16. Various means can be used to attach sampler 12 to post 16 including arm members which extend out from the post, a bracket arrangement and the like. Post 16 is secured to a flat base 18 such that a multi-well tray 20 can be positioned beneath sampler 12. Tray 20 typically has 96 wells, although trays having different number of wells are also within the scope of this invention. Into each of these wells 22 a culture can be grown in microliter quantities. Alternately, test tubes could be placed into each of the wells 22 and the liquid placed in each of the tubes. A control member is used to raise and lower the sampler 12 such that it can be positioned directly on top of the tray 20. As more fully described hereinbelow, a suction pump or other similar means for creating a vacuum in the sampler 12 is joined to the sampler 12 such that predetermined quantities of fluid from each of the wells 22 can be withdrawn into the sampler 12. Such sample can then be placed into an empty tray or into a tray in which a different culture or other material is contained.

Referring now to FIGS. 2, 3 and 4, the sampler 12 is more clearly illustrated. The sampler 12 is comprised of a clear plastic housing 28 having a generally rectangular configuration. Typically, it has a generally flat top 30, flat sides and ends 32, 34 such that a box-like structure is created. A skirt 36 is circumferentially disposed about the housing 28 in a configuration such that, if the pipette tips hereinbelow described are not used, skirt 36 would matingly engage the sides of an associated tray 20. Skirt 36 preferably extends about the sides and ends of the tray 20 such that samples are exposed as little as possible to the ambient during the sampling procedure.

A plate 38 is disposed within the housing 28, and is joined to the sides and ends 32, 34. Plate 38, along with sides and ends 32, 34 and top 30 form a first manifold chamber 39. Extending from plate 38 are a plurality of connector conduits 40. Inasmuch as the usual tray 20 includes 96 wells, 96 collector conduits 20 would be positioned on plate 38. Collector conduit 40 includes a first portion 42 and second portion 44. First portion 42 depends down from plate 38 and is configured to engage an associated pipette tip as hereinbelow described in greater detail. Second portion 44 formed of inclined walls 45, extends up from plate 38 into the chamber 39. A first opening 46 formed on the first portion 42 has an inner diameter of approximately 0.088 inches ±20%. The outer diameter of the first portion 42 adjacent opening 46 is approximately 0.22 inches ±20%. It has been found that an opening 46 of this size is sufficient to withdraw the desired amount of fluid. Second portion 44 defines an upper opening 50 which has an inner diameter of approximately 0.032 inches ±20%. Thus, opening 50 is substantially smaller than opening 46. Opening 50 is chosen such that filling the conduit 40 to the opening 50 provides a precise measurement. Excess filling results in an overflow of liquid into chamber 39 such that the contents of the conduit 40 remains constant, thus insuring transfer of a precise volume of liquid. This feature is believed to be unique to the conical shape design of the conduit 40 which also prevents mixing of the liquid in adjacent conduits 40 should overflow occur. As illustrated, the internal walls from opening 46 to opening 50 can be tapered.

Depending from and joined to the collector conduits 40 is a series of pipette tips 60. Pipette tips 60 include a first portion 62 configured to circumferentially surround and engage the first portion 42 of the collector conduits 40. Tips 60 also include a tapered second portion 64 which extends into the well of an associated tray 20. As shown in FIG. 2, the internal walls of each of the pipette tips 60 are tapered such that the large diameter portion is adjacent the collector conduits 40 and the smaller diameter portion is inserted into the associated tray 20.

In the preferred embodiment pipette tips 60 are joined together in a mutually separated, axially parallel spaced relationship by a network of integral web-like links 68. This enables the patterned array of tips 60 to be easily joined to and removed from the array of collector conduits 40. To aid in this procedure, extending tabs 70 are joined to the patterned array of tips 60 as illustrated in FIG. 2.

To prevent the each tip 60 from being inserted too far into an associated well and engaging the bottom of the well, a series of annular rings 72 are disposed about selected tips 60. Rings 72 engage the tray 20 and support the bottom of each tip 60 slightly about the bottom of an associated well 22.

Rather than an interconnected patterned array of tips 60 as shown in FIG. 2, individual collector tips may be used. In such an environment, the problem becomes the means for easily joining the tips 60 to the array of collector conduits 40 and removal therefrom. One means for joining separate tips 60 to the conduits 40 is shown in FIG. 3, in which a plate 74 has a series of openings 76 into which the various separate tips 60 can be placed. Once all of the tips 60 are arranged on plate 74, one need only press the sampler 12 towards the plate 74 so as to firmly engage each of the tips 60 about an associated conduit 40.

Referring now to FIG. 4, removal of the individual tips 60 can be accomplished by providing another plate 78 which also includes a series of openings 80. In such embodiment, each of the tips 60 may include an outwardly extending protrusion 82 which can be forced through opening 80. Upon withdrawal of sampler 12, the protrusion 80 would engage the bottom of plate 80 and thus the tips 60 would be captured in or beneath plate 78. Tips 60 can be completely removed from plate 78 by pushing plate 78 away from sampler 12.

METHOD OF OPERATION

In a typical setting, sampler 12 would be contained in a sterile package. The package would be opened and the sampler 12 fitted with an associated array of pipette tips 60. Tips 60, which may be joined together as illustrated in FIG. 2, may also be packaged in a sterile manner. Tabs 70 enable the entire array of tips 60 to be easily joined to or removed from conduits 40 in a manner which maintains a high degree of sterility. Sampler 12 and tips 60 would then be placed on stand 14 directly above the tray 20 such that the 96 collector conduits 40 and tips 60 are each above an associated well 22. A suction hose is joined to port 35 in flow communication with chamber 39 and a suction is applied with a 20 mil syringe withdrawn to 10 ml. In this manner, fluid is drawn through the openings in tips 60 and conduits 40. The flow is stopped when the liquid reaches opening 50.

To transfer the liquid from the sampler 12, the filled sampler 12 is lowered into another tray and the syringe plunger is depressed to zero. This procedure releases the contained volume into the tray. Sampler 12 can also be set on a tray which is not divided into individual wells, but contains liquid which is used to feed or to be transferred to a 96 well micro-plate. The sampler 12 thus has multiple function and is unique in its diversity.

After the sample is obtained and transferred, the suction hose can be removed and the sampler 12 and tips 60 discarded. However, since tips 60 can be easily removed, in some embodiments it may be appropriate to remove and discard only tips 60. Upon completion of the transfer, a cover can be placed on the tray 20 to avoid contamination. Thus, 96 separate specimens are readily transferred from one tray to another in a straight forward manner and without a complex device such as those shown by the prior art.

Because the sampler 12 and associated system of the present invention is staight forward in-its construction, it is particularly adapted to situations where single use is desired.

While this invention has been described in its preferred embodiment, it is to be expressly understood that the words which have been used are words of description rather than limitation, and the changes within the perview of the appended claims may be made without departing from the true spirit and scope of the invention in its broader aspects.

I claim:

1. A pipette sampler system for removing a plurality of liquid samples from a multi-well tray, comprising:
   a housing having a main body portion and a plurality of elongated, outwardly extending collector conduits with a first portion of each conduit configured to be inserted into an associated pipette tip, and a second portion extending into the main body of said housing, said first and second portions having co-axial openings for fluid flow, said opening for fluid flow in said first portion being larger than said opening for fluid flow in said second portion;
   a patterned array of tubular pipette tips removably joined to and in flow communication with said array of collector conduits; and
   means for forming a vacuum in said housing whereby a predetermined quantity of liquid flows into said pipette tips and said collector conduits.

2. A pipette sampler system according to claim 1 wherein each said pipette tip includes a cylindrical portion configured to circumferentially engage an associate collector conduit.

3. A pipette sampler system according to claim 1 further including web-like members joining said pipette tips together in a spaced, generally parallel array.

4. A pipette sampler system according to claims 1 or 3 further including means for removing said pipette tips from said collector conduits.

5. A pipette sampler system according to claim 4 where said removing means comprises at least one outwardly extending tab.

6. A pipette sampler system according to claim 4 wherein said removing means comprises a plate having a series of openings, said pipette tips passing through said openings and engaging said plate such that said pipette tips are retained in said plate.

7. A pipette sampler system according to claim 1 further including spacer means for engaging said multi-well trays and thereby limiting the distance into each well a pipette tip may extend.

8. A pipette sampler system for removing a plurality of liquid samples from a multi-well tray, comprising:
   a housing having a top member, side and end members, and a generally flat plate joined to said side and end members, said plate along with said top, side and end members defining a first manifold chamber;
   a plurality of elongated, outwardly extending collector conduits with a first portion of each conduit configured to be inserted into an associated pipette tip, and a second portion extending into said first manifold chamber, said first and second portions having co-axial openings for fluid flow, said opening for fluid flow in said first portion being larger than said opening for fluid flow in said second portion;
   a patterned array of tubular pipette tips removably joined to and in flow communication with said collector conduits; and
   a port on said housing in flow communication with said first manifold chamber whereby a vacuum can be created in said first manifold chamber causing a predetermined quantity of liquid to flow into said pipette tips and said collector conduits.

9. A pipette sampler system according to claim 8 wherein each said pipette tip has a first generally cylindrical section configured to circumferentially engage said first portion of an associated collector conduit, and a second tapered section for insertion into an associated well on said multi-well tray.

10. A pipette sampler system according to claims 8 or 9 further including web-like members joining said pipette tips together in a spaced, generally parallel array.

11. A pipette sampler system according to claim 10 further including means for removing said pipette tips from said collector conduits.

12. A pipette sampler system according to claim 11 wherein said removing means comprises a plate having a series of openings, said pipette tips passing through said openings and engaging said plate such that said pipette tips are retained in said plate.

13. A pipette sampler system according to claim 12 wherein each said pipette tip including protuberance means for engaging said plate.

* * * * *